United States Patent
Barnes et al.

(10) Patent No.: US 10,195,451 B2
(45) Date of Patent: Feb. 5, 2019

(54) MEDICAL DEVICE WITH LACK-OF-READINESS ALARM

(71) Applicant: Physio-Control, Inc., Redmond, WA (US)

(72) Inventors: Angela D. Barnes, Kent, WA (US); Matthew Lawrence Bielstein, Renton, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 0 days.

(21) Appl. No.: 15/194,296

(22) Filed: Jun. 27, 2016

(65) Prior Publication Data

US 2016/0303390 A1 Oct. 20, 2016

Related U.S. Application Data (62) Division of application No. 13/662,292, filed on Oct. 26, 2012, now Pat. No. 9,375,584.

(60) Provisional application No. 61/650,406, filed on May 22, 2012.

(51) Int. Cl.
*A61N 1/39* (2006.01)

(52) U.S. Cl.
CPC .......... *A61N 1/3925* (2013.01); *A61N 1/3993* (2013.01)

(58) Field of Classification Search
CPC .................................................. A61N 1/3925
USPC ........................................................ 607/6, 7
See application file for complete search history.

(56) References Cited

U.S. PATENT DOCUMENTS

| | | | |
|---|---|---|---|
| 5,697,955 A | 12/1997 | Stolte | |
| 6,246,907 B1 | 6/2001 | Lin et al. | |
| 6,366,809 B1 | 4/2002 | Olson et al. | |
| 8,086,306 B2 | 12/2011 | Katzman et al. | |
| 2004/0133244 A1* | 7/2004 | Vaisnys | A61N 1/39 607/5 |
| 2005/0015115 A1 | 1/2005 | Sullivan et al. | |
| 2005/0246199 A1 | 11/2005 | Futch | |
| 2005/0273023 A1 | 12/2005 | Bystrom et al. | |
| 2006/0149323 A1 | 7/2006 | Merry et al. | |
| 2008/0136652 A1 | 6/2008 | Vaisnys et al. | |
| 2008/0139954 A1 | 6/2008 | Day et al. | |
| 2011/0288604 A1 | 11/2011 | Kaib et al. | |

FOREIGN PATENT DOCUMENTS

FR 2917298 A1 12/2008

OTHER PUBLICATIONS

European International Search Report and Written Opinion dated Jul. 26, 2013, 11 pages.

* cited by examiner

*Primary Examiner* — Alyssa M Alter
(74) *Attorney, Agent, or Firm* — Lane Powell PC

(57) ABSTRACT

A medical device for caring for a patient includes a patient utility for measuring a patient parameter or administering a therapy to the patient and an alarm system that has a receiver to accept status information about the medical device. A use detector of the alarm system is structured to determine when the medical device is being prepared for use and a status detector of the alarm system is adapted to determine from the status information that the medical device is in a ready state. The alarm system further includes an alarm that is activated when the medical device is both being prepared for use and not in the ready state. This description also includes methods of generating an alarm when the medical device is both being prepared for use and not in the ready state.

14 Claims, 7 Drawing Sheets

MEDICAL DEVICE WITH ALARM SYSTEM

FIG. 1  *DEFIBRILLATION SCENE*

| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |

FIG. 2  *TWO MAIN TYPES OF EXTERNAL DEFIBRILLATORS*

FIG. 3

COMPONENTS OF EXTERNAL DEFIBRILLATOR

FIG. 4   *MEDICAL DEVICE WITH ALARM SYSTEM*

FIG. 5 *EXAMPLE SIMPLE USER INTERFACE OF ALARM FOR MEDICAL DEVICE*

FIG. 6  *EXAMPLE USER INTERFACE OF ALARM FOR MEDICAL DEVICE*

FIG. 7   *COMPONENTS OF ALARM SYSTEM*

FIG. 8

*METHOD FOR ALERTING ABOUT READY STATE OF MEDICAL DEVICE*

MEDICAL DEVICE WITH LACK-OF-READINESS ALARM

CROSS REFERENCE TO RELATED PATENT APPLICATIONS

This patent application is a division of co-pending U.S. patent application Ser. No. 13/662,292, filed on Oct. 26, 2012, entitled MEDICAL DEVICE WITH LACK-OF-READINESS ALARM, which claims the benefit to U.S. Provisional Patent Application Ser. No. 61/650,406, filed on May 22, 2012, entitled LACK-OF-READINESS ALARM FOR MEDICAL DEVICE ABOUT TO BE USED, the disclosures of both of which are hereby incorporated by reference for all purposes.

FIELD

This invention generally relates to medical devices such as external defibrillators.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and, if not treated, death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrhythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them.

During VF, the person's condition deteriorates, because the blood is not flowing to the brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved. Indeed, for patients with an extended down-time, survival rates are higher if CPR is administered prior to defibrillation.

Advanced medical devices can actually coach a rescuer who performs CPR. For example, a medical device can issue instructions, and even prompts, for the rescuer to perform CPR more effectively.

Many medical devices include or use components that are subject to ageing or expiration. For example, many defibrillators use gelled pads that dry over time and become unusable. Additionally, portable defibrillators include batteries to generate shock signals and operate the defibrillator, and such batteries may be unable to store adequate charge due to ageing. In other cases the batteries may be physically sound but merely store a charge that is below that necessary to properly operate the defibrillator. In such instances, a rescuer or other person may take a medical device into a rescue situation when the medical device is not in proper condition for use due to the battery not being charged, or consumable or other components not being ready for use.

Embodiments of the invention address these and other limitations of the prior art.

BRIEF SUMMARY

The present description gives instances of medical devices, systems, and methods, the use of which may help overcome problems and limitations of the prior art. In one embodiment, a medical device includes a patient utility for measuring a patient parameter or administering a therapy to the patient as well as an alarm system. The alarm system includes a receiver to accept status information about the medical device, a use detector structured to determine when the medical device is being prepared for use, a status detector adapted to determine from the status information that the medical device is in a ready state, and an alarm that is activated when the medical device is both being prepared for use and not in the ready state. The alarm may be user configurable.

Other embodiments include methods for alerting a user of a medical device to a state of readiness of the medical device. Methods may include sensing that the medical device is about to be used and assessing a value for a readiness state of the medical device. When it is determined that the medical device is about to be used and the assessed readiness state value is below a threshold level, then an alarm is generated that alerts the user to the status of the medical device.

An advantage over the prior art is that it reduces or eliminates the possibility of a rescuer bringing a medical device to a rescue scene that may not function correctly or to its full capabilities.

These and other features and advantages of this description will become more readily apparent from the following Detailed Description, which proceeds with reference to the drawings, in which:

BRIEF DESCRIPTION OF THE DRAWINGS

FIG. 2 is a table listing two main types of the external defibrillator shown in FIG. 1, and who they might be used by.

DETAILED DESCRIPTION

Figure 1:
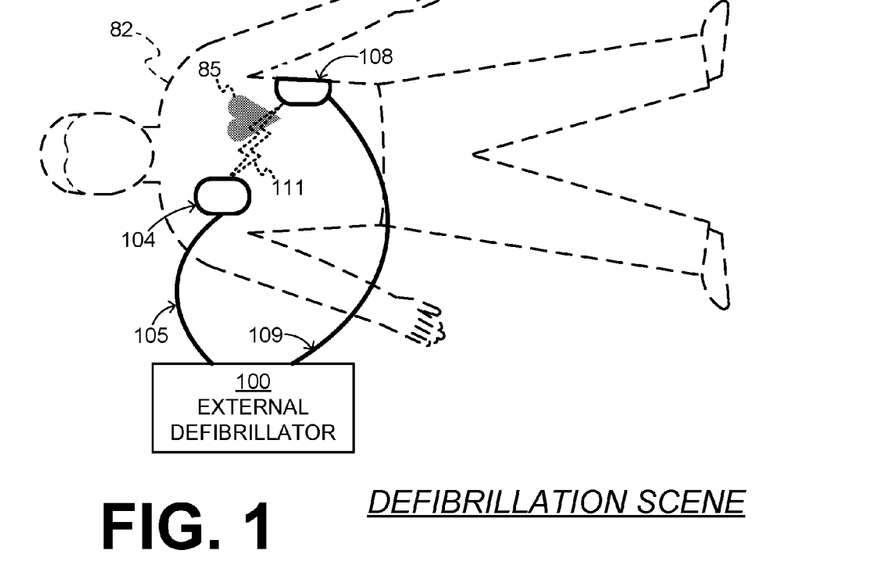
FIG. 1 is a diagram of a scene where an external defibrillator is used to save the life of a person according to embodiments.

FIG. 1 is a diagram of a defibrillation scene. A person 82 is lying on their back. Person 82 could be a patient in a hospital, or someone found unconscious, and then turned to be on their back. Person 82 is experiencing a condition in their heart 85, which could be Ventricular Fibrillation (VF).

A portable external defibrillator 100 has been brought close to person 82. At least two defibrillation electrodes 104, 108 are usually provided with external defibrillator 100, and are sometimes called electrodes 104, 108. Electrodes 104, 108 are coupled with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, goes also through heart 85, in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

Figure 2:
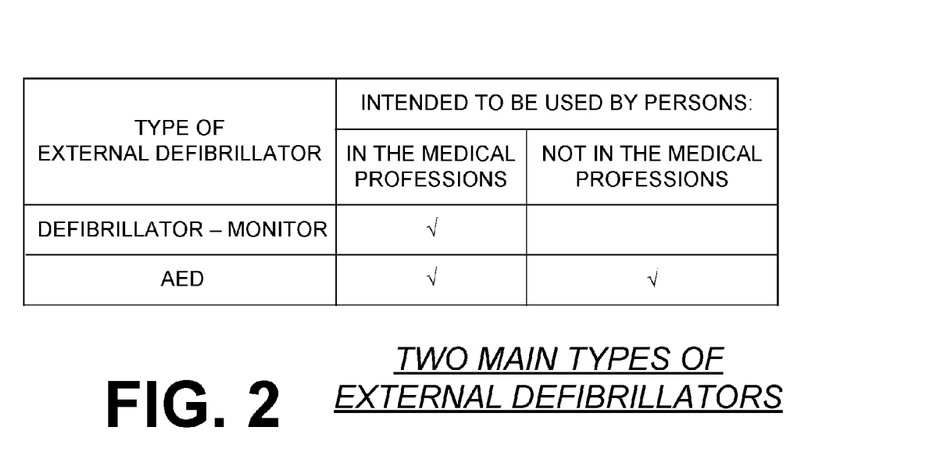

FIG. 2 is a table listing two main types of external defibrillators, and who they are primarily intended to be used by. A first type of defibrillator 100 is generally called a defibrillator-monitor, because it is typically formed as a single unit in combination with a patient monitor. A defibrillator-monitor is sometimes called monitor-defibrillator. A defibrillator-monitor is intended to be used by persons in the medical professions, such as doctors, nurses, paramedics, emergency medical technicians, etc. Such a defibrillator-monitor is intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/AED training on their own initiative. This way, defibrillation can be administered soon enough after the onset of VF, to hopefully be effective in rescuing the person.

There are additional types of external defibrillators, which are not listed in FIG. 2. For example, a hybrid defibrillator can have aspects of an AED, and also of a defibrillator-monitor. A usual such aspect is additional ECG monitoring capability.

Figure 3:
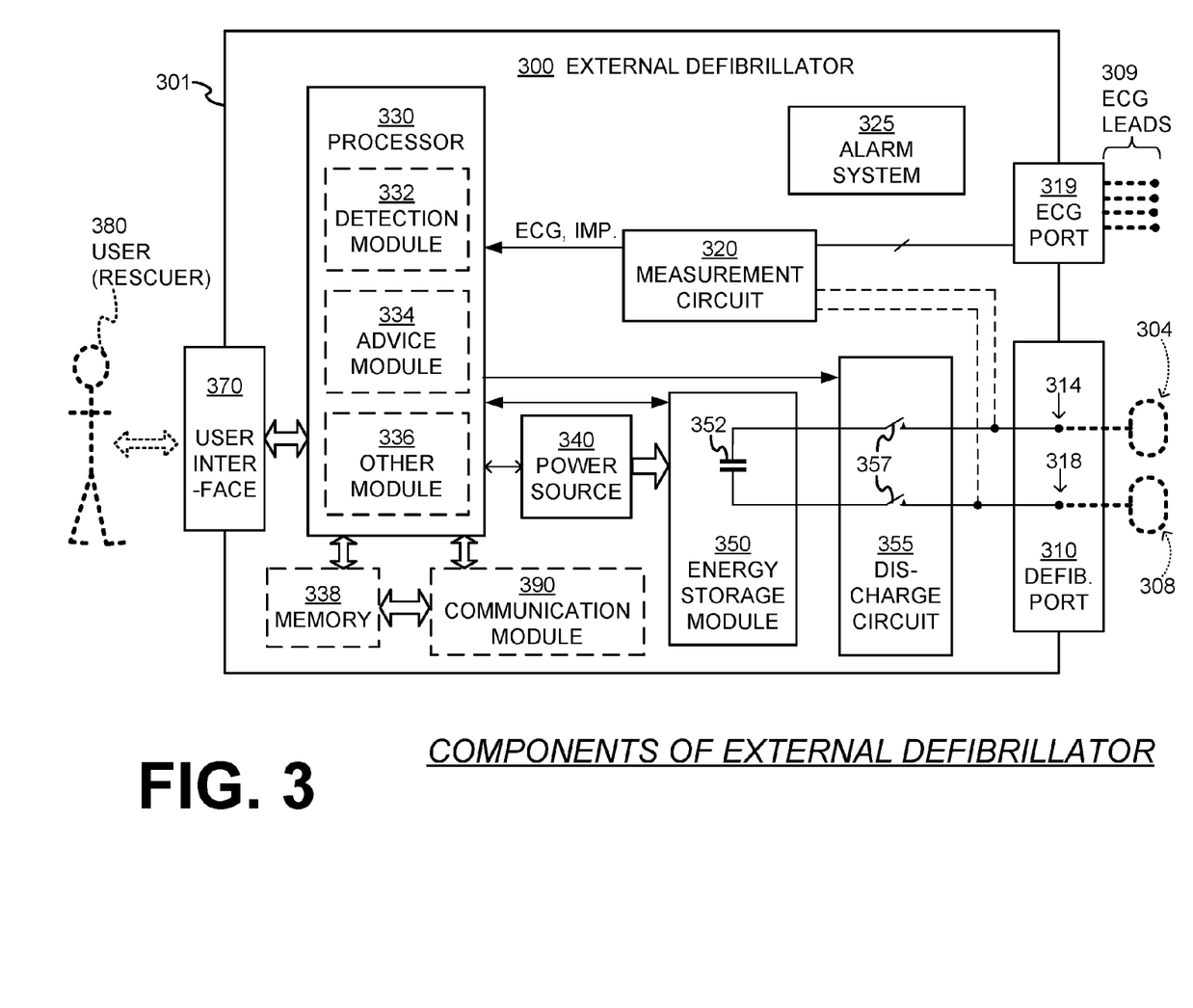
FIG. 3 is a diagram showing components of an external defibrillator medical device, such as the one shown in FIG. 1, which includes an alarm system according to embodiments.

FIG. 3 is a diagram showing components of an external defibrillator 300 made according to embodiments. These components can be, for example, in external defibrillator 100 of FIG. 1. Plus, these components of FIG. 3 can be provided in a housing 301, which is also known as casing 301.

External defibrillator 300 is intended for use by a user 380, who would be the rescuer. Defibrillator 300 typically includes a defibrillation port 310, such as a socket in housing 301. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored in defibrillator 300, as will be seen later in this document.

If defibrillator 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or from a different number of leads. Moreover, a defibrillator-monitor could have additional ports (not shown), and an other component 325 for the above described additional features, such as patient signals.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions.

In addition, the defibrillator 300 may include an alarm system 325 that operates to alert an operator if the defibrillator 300 is about to be used but is not ready for use, as described in detail below.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, and so on.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for user 380. User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

As has been mentioned, the present description is about devices, control systems, and methods for a medical device with a lack-of-readiness alarm.

Embodiments are now described in more detail.

Figure 4:
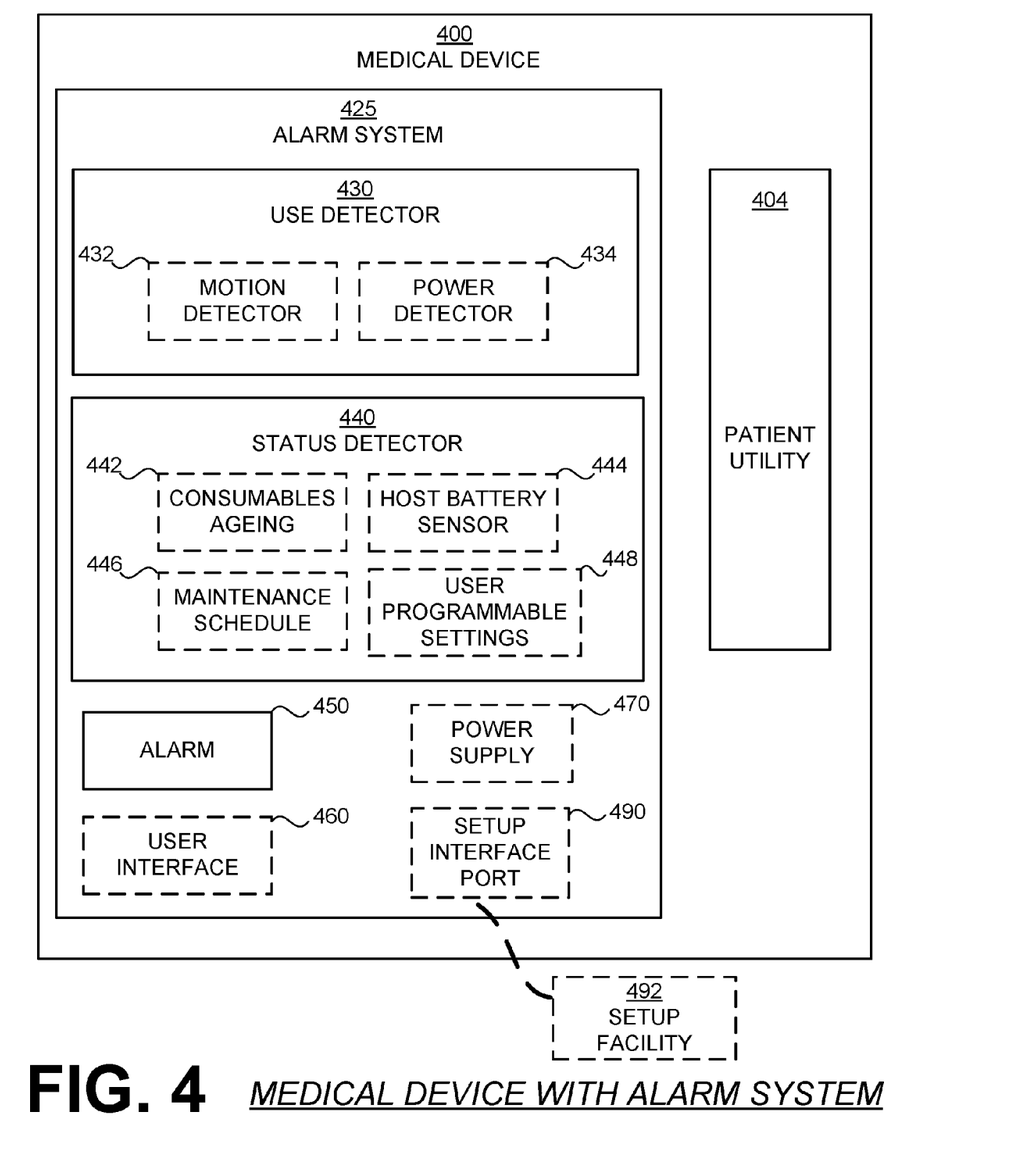
FIG. 4 is a functional block diagram of an alarm system component of the medical device of FIG. 3 according to embodiments.

FIG. 4 is a functional block diagram of an alarm system component of a medical device 400 according to embodiments. The medical device 400 may be the same or similar to the defibrillator 300 of FIG. 3. The medical device 400 is one for caring for a patient, for example the patient 82 of FIG. 1. The medical device 400 includes a patient utility 404 for measuring a patient parameter or administering a therapy to the patient 82. The therapy may be defibrillation for example. The measured parameters may include, for example, a person's full ECG (electrocardiogram) signals, or impedance between two electrodes. Additionally, these parameters may be signals about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

The medical device 400 also includes an alarm system 425 that functions to generate an alarm under certain conditions. The alarm system 425 includes a receiver such as a status detector 440 to accept status information about the medical device 400 that includes the alarm system 425. In some embodiments the status detector 425 includes a battery sensor 444 structured to determine a charge level of a battery in the medical device 400. In other embodiments the status detector 440 includes a consumables ageing component 442 structured to determine if an age of any consumable of the medical device 400 is beyond a respective expiration date. Consumables of the medical device 400 may include pads, leads, batteries, etc., each of which may include a specific and unique expiration date. In other embodiments the status detector 440 includes a maintenance schedule component 446 structured to determine if the medical device 400 or components thereof is beyond a service date. Service dates may include dates for software updates, for example. In each of these examples, the status detector 440 may be structured to determine that the medical device 400 is in the ready state when the particular component 442, 444, 446 satisfies its own criteria. For example, the status detector 440 may determine that the medical device is in a ready state when the consumables ageing component 442 determines that no age of any consumable of the medical device 400 is beyond its respective expiration date. Similarly, the status detector 440 may determine that the medical device 400 is in a ready state when the battery sensor 444 that a charging level of the medical device is above a threshold level. Further, the status detector 440 may include user programmable settings 448 so that a user may set conditions for which the alarm system 425 would trigger an alarm to alert the user. When the user sets his or her own user programmable settings 448, the status detector 440 modifies the ready-state determination based on the user programmable settings. Functions of the status detector 440 may be effected by functions of a microprocessor of the medical device 400.

The alarm system 425 also includes a use detector 430 structured to determine when the medical device is being prepared for use. For example the detector 430 may include a motion detector component 432 for generating a motion signal when the medical device is moved. The motion detector 432 may be an accelerometer, for instance, that generates a signal when the medical device 400 is moved, for example when a rescuer picks up the medical device 400 to take to a rescue scene. The use detector 430 may also include a power detector component 434 structured to generate a remove signal when the medical device is separated from a power source that is external to the medical device. In other words, if the medical device 400 is plugged into wall power, the power detector component 434 generates a signal when the medical device is unplugged, which may indicate that the medical device is being prepared for use. Functions of the use detector 430 may be effected by functions of a microprocessor of the medical device 400.

In some embodiments the alarm system 425 may include its own power supply 470, separate from any power supply on the medical device 400.

The alarm system 425 of the medical device 400 further includes an alarm 450 that is activated when the medical device is both being prepared for use and not in the ready state. For instance, the alarm system 425 generates an alarm when the medical device 400 is unplugged, but when pads associated with the medical device are beyond their use date. This gives the rescuer notice that he or she will need to replace the pads before the medical device 400 is properly ready for use. Providing such an alarm 450 when it is detected that the medical device 400 is being readied for use is much better than those systems without alarms, in which case the rescuer may take the medical device into the field with inadequate equipment. The alarm 450 may be visible, audible, haptic, or any combination thereof. Additionally the audible alarm 450 may include vocalizing at least one word, which may be a word or words of caution or a warning. The audible alarm may present vocally to the user the reasons for which the alarm 450 is activated.

Figure 5:
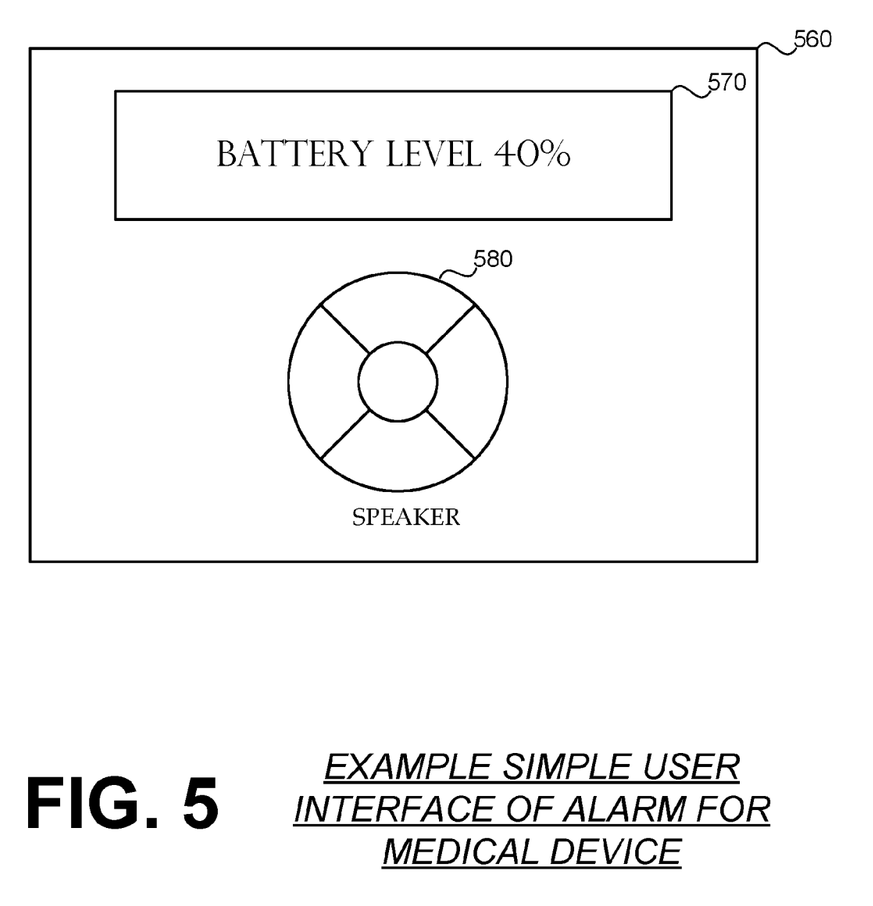
FIG. 5 is a block diagram of an example simple user interface for the alarm system of FIG. 4 according to embodiments.

The alarm system 425 may include a user interface 460 including a user input for causing the use detector 430 to determine that the medical device is being prepared for use in response to receiving a manually generated input at the user input. FIG. 5, for example, illustrates an example user interface 560. The user interface 560 includes a screen 570 on which information may be displayed. 5. The screen 570 may be used to communicate one or more reasons that caused the alarm 450 to be activated. For example the screen 570 may display text or symbols for communicating to the user. The user interface 560 also includes an audible interface such as a speaker 580, which may produce sounds or voice commands for the user of the medical device 400, such as those described above.

Figure 6:
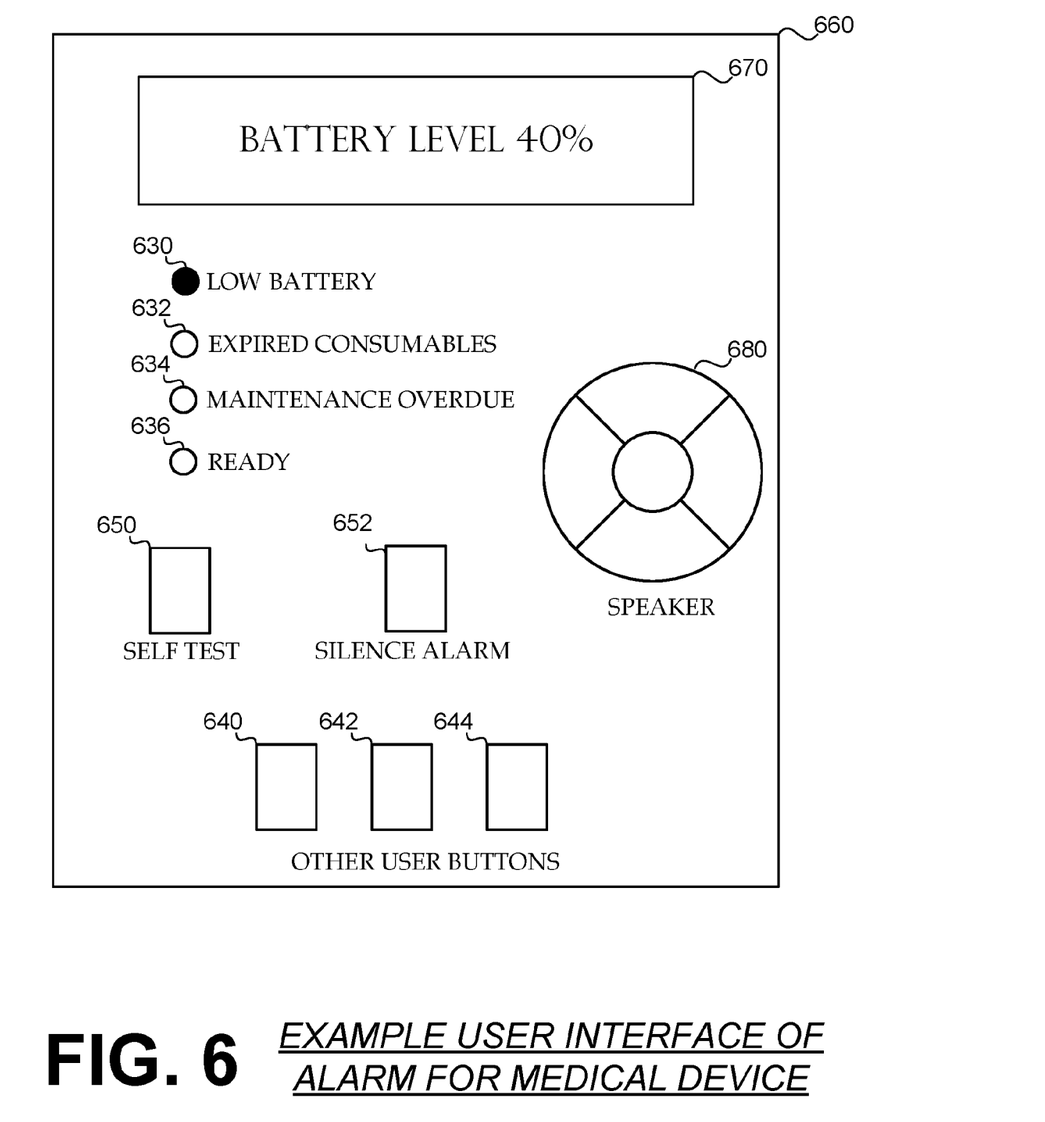
FIG. 6 is a block diagram of an example user interface for the alarm system of FIG. 4 according to embodiments.

FIG. 6 illustrates another example user interface 660, which may be an embodiment of the user interface 460 of FIG. 4. The user interface 660 of FIG. 6 includes a screen 670 and speaker 680, similar to the user interface 560 of FIG. 5. The user interface 660 includes further features for user interaction, however. Indicators 630, 632, 634, and 636 may illustrate a status of the medical device 400. For example, when the alarm system 425 determines that the device is about to be used and the battery level has an insufficient charge, an alarm may sound from the speaker 680 and the indicator 630 turns on or flashes to inform the user that the medical device is not in a ready state. The indicator 632 generates a signal when one or more of the consumables of the medical device 400 have expired or are nearing expiration. The indicator 634 generates a signal when maintenance is overdue. Differently, the indicator 636 may generate a ready signal if the alarm system 425 determines that the medical device is ready to be used and the medical device 400 is, in fact, ready for use. For example the ready signal may be generated through indicator 636 when the medical device 400 is ready to be used, the batteries are fully charged, the medical device has up-to-date software, and all of the consumables are within their usable period.

The user interface 660 may include buttons for user feedback, such as a button 650 that causes the alarm system to execute a self-test to determine, if the medical device 400 were to be used, the condition of the medical device. A button 652 may allow the user to silence the alarm 450 generated by the alarm system 425. In other embodiments the alarm 450 may be automatically silenced after a pre-set time. In further embodiments the alarm 450 may be automatically re-armed after a time duration.

Of course other user buttons, such as the user buttons 640, 642, 644, or feedback signals may be included in the user interface 660. This may allow the user to program certain desired functions into the medical device, for example user programmable settings 448 for a particular situation. In other embodiments the user programmable settings 448 may be entered or modified using a setup facility 492, which may be coupled to the medical device 400 or alarm system 425 through a setup interface port 490 when needed. The setup facility 492 may be a program operating on a computer coupled to the medical device 400.

Figure 7:
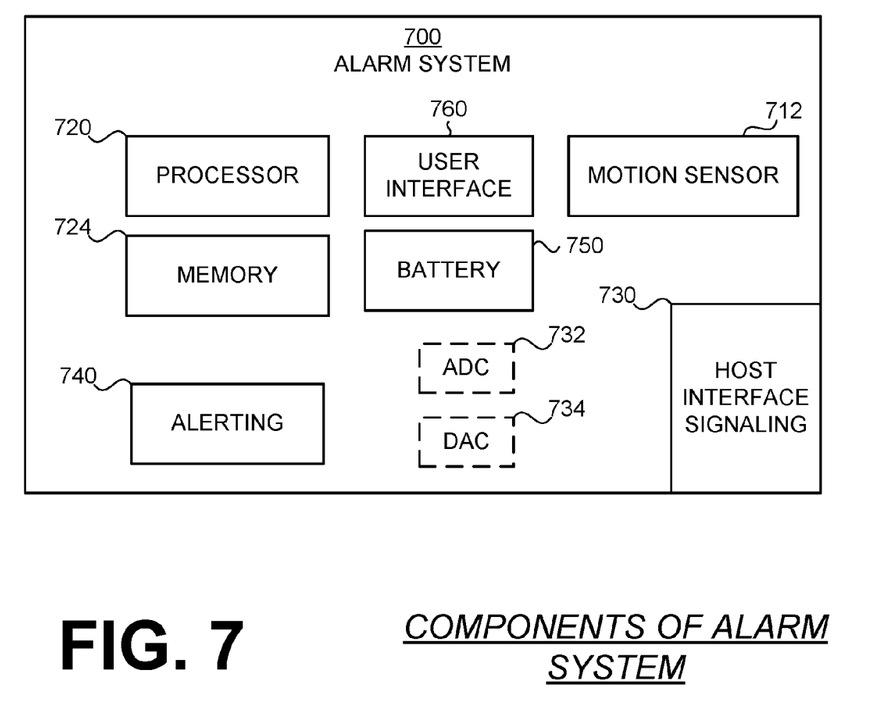
FIG. 7 is a block diagram illustrating example components that may be used to construct the alarm system of FIG. 4 according to embodiments.

FIG. 7 is a block diagram illustrating example components of an alarm system 700 that may be used to construct the alarm system 425 of FIG. 4 according to embodiments. The alarm 700 may be formed on a circuit board, for example, which may be coupled to or mounted within a medical device. The alarm system 700 may be powered by a battery 750, which may be a long-life user replaceable lithium coin cell, for example.

A processor 720 may be programmed to produce many or all of the functions of the alarm system 425 described above. Such programs may be stored in memory 724, for instance, or may be entered by use of a user interface 760, or through a setup facility such as the setup facility 492 of FIG. 4.

An alerting facility 740 may be used to perform the functions of generating the alarm for the user. The alerting facility 740 may include generating signals for a user interface 760, which may be an example of the user interfaces 560, 660 described above. The alerting facility 740 may also be embodied by a vibrating motor or piezoelectric buzzer, for example. A motion sensor 712 may be embodied by an accelerometer or other appropriate device. A host interface 730 may receive signals or data from the medical device to which the alarm system 700 is attached. The signals may be in analog or digital form.

Converters, such as an analog-to-digital converter 732 or digital-to-analog converter 734 may be used to convert signals from one domain to the other. Signals for conversion may include signals from the motion sensor 712 or signals received through the host interface 730, for instance, or for other signals used to help the alarm system 700 operate properly.

Figure 8:
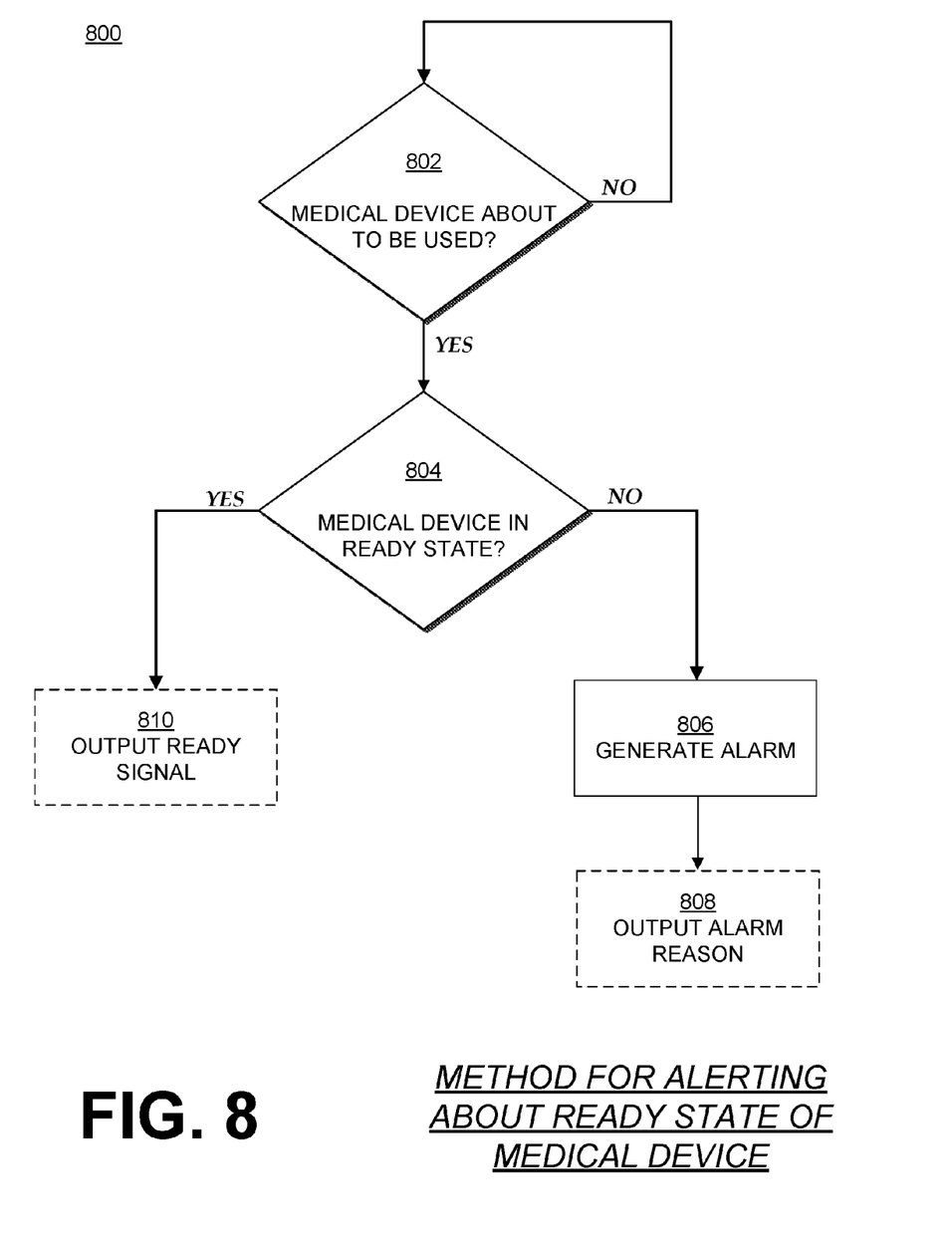
FIG. 8 is a flowchart illustrating example methods according to embodiments.

FIG. 8 shows a flowchart 800 illustrating example methods for alerting a user of a medical device to a state of readiness of the medical device according to embodiments. According to an operation 802, an alarm system determines if a medical device to which it is connected is about to be used. Sensing that the medical device is about to be used may include sensing that the medical device has moved, or may include sensing that the medical device has been separated from a power source external to the medical device.

When the alarm system determines that the medical device is about to be used, an operation 804 assesses a value for a readiness state of the medical device. The value may be numeric or a Boolean value, for example.

An operation 806 generates an alarm when the medical device is about to be used and the assessed readiness state value is below a threshold level. Assessing a value for a readiness state may include determining an age of at least one consumable device used in association with the medical device, such as pads or batteries. The assessment may also include determining a charge level of the battery. The assessment may also include determining how recently the medical device has been serviced or updated, such as by accessing a maintenance log of the medical device.

An optional operation 808 may output the cause of the alarm to the user. For example, the method may show the cause of the alarm on a display, or may turn on an indicator light, for example. In another optional operation 810, the method outputs a ready signal when the medical device is about to be used and the medical device is at or above the threshold level of readiness.

The threshold level used in operation 804 to compare to the readiness state value of the medical device may be programmable and set by a user. The user may also be able to select factors that determine the readiness state. Such factors may include, for example, battery power of the medical device, age of consumables to be used in conjunction with the medical device. Other factors may include a maintenance log of the medical device, or other indications of whether the medical device is up-to-date. For instance, the user may select which of the monitored conditions will be used in the alarm analysis.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems.

The following claims define certain combinations and subcombinations of elements, features, steps, and/or functions, which are regarded as novel and non-obvious. Additional claims for other combinations and subcombinations may be presented in this or a related document.

In the claims appended herein, the applicant invokes 35 U.S.C. § 112, paragraph 6 only when the words "means for" or "steps for" are used in the claim. If such words are not used in a claim, then the inventor does not intend for the claim to be construed to cover the corresponding structure, material, or acts described herein (and equivalents thereof) in accordance with 35 U.S.C. § 112, paragraph 6.

What is claimed is:

1. A method for alerting a user of a medical device to a state of readiness of the medical device, the method comprising:
   detecting that the medical device is about to be used for one or both of patient monitoring or patient treatment, the detecting including at least one of detecting that the medical device has moved or detecting that the medical device has been separated from a power source external to the medical device;
   initiating an assessment of the medical device in response to detecting that the medical device is about to be used for the one or both of patient monitoring or patient treatment, the assessment to determine a value for a readiness state of the medical device; and
   generating an alarm when the assessed readiness state value of the medical device is below a threshold level.

2. The method of claim 1, further comprising:
   outputting a cause of the alarm.

3. The method of claim 1, further comprising:
   outputting a ready signal when the medical device is at or above the threshold level of readiness.

4. The method of claim 1, in which
   the medical device comprises a user interface, and further comprising setting the threshold level by accepting input through the user interface.

5. The method of claim 1, in which
   the medical device comprises a user interface, and further comprising receiving from a user a selection of one or more factors used to determine the readiness state through the user interface.

6. The method of claim 1, further comprising
   setting the threshold level by accepting input through a user interface.

7. The method of claim 1 in which
   initiating an assessment of the medical device to determine a value for a readiness state comprises determining an age of at least one consumable device used in association with the medical device.

8. The method of claim 1 in which
   initiating an assessment of the medical device to determine a value for a readiness state comprises determining a charge level of a battery of the medical device.

9. The method of claim 1 in which
   initiating an assessment of the medical device to determine a value for a readiness state comprises accessing a maintenance log of the medical device.

10. A method for alerting a user of a medical device to a state of readiness of the medical device, the method comprising:
    accepting at a user interface a user input to set one or more conditions to trigger a state of readiness alarm for the medical device;
    setting the one or more conditions as one or more triggers for the state of readiness alarm for the medical device;
    detecting that the medical device is being prepared for use for one or both of patient monitoring or patient treatment, the detecting including at least one of detecting that the medical device has been moved or detecting that the medical device has been separated from a power source external to the medical device;
    initiating an assessment of the medical device in response to detecting that the medical device is being prepared for the use for one or both of patient monitoring or patient treatment, the assessment to determine a readiness value of the medical device that includes a comparison of an age of consumable component of the medical device to an expiration date of the consumable component of the medical device; and
    generating an alarm when the readiness value of the medical device is below a threshold level defined by at least one of the one or more triggers.

11. The method of claim 10, further comprising:
    outputting a cause of the alarm.

12. The method of claim 10, further comprising:
    changing the threshold level by accepting further input through the user interface.

13. The method of claim 10 in which
    initiating an assessment of the medical device to determine a readiness value of the medical device comprises determining a charge level of a battery of the medical device.

14. The method of claim 10 in which
    initiating an assessment of the medical device to determine a readiness value of the medical device comprises accessing a maintenance log of the medical device.

* * * * *